(12) United States Patent
Butts et al.

(10) Patent No.: US 8,728,440 B2
(45) Date of Patent: May 20, 2014

(54) NANOPARTICULATE COMPOSITIONS FOR DIAGNOSTIC IMAGING

(75) Inventors: Matthew David Butts, Rexford, NY (US); Peter John Bonitatibus, Jr., Saratoga Springs, NY (US); Robert Edgar Colborn, Niskayuna, NY (US); Andrew Soliz Torres, Troy, NY (US)

(73) Assignee: General Electric Company, Niskayuna, NY (US)

( * ) Notice: Subject to any disclaimer, the term of this patent is extended or adjusted under 35 U.S.C. 154(b) by 7 days.

(21) Appl. No.: 13/592,853

(22) Filed: Aug. 23, 2012

(65) Prior Publication Data

US 2014/0056819 A1    Feb. 27, 2014

(51) Int. Cl.
*A61K 49/18* (2006.01)
*B82Y 5/00* (2011.01)
*A61K 49/04* (2006.01)

(52) U.S. Cl.
CPC .............. *A61K 49/1848* (2013.01); *B82Y 5/00* (2013.01); *A61K 49/04* (2013.01)
USPC .............................. 424/9.3; 424/489; 424/9.1

(58) Field of Classification Search
None
See application file for complete search history.

(56) References Cited

U.S. PATENT DOCUMENTS

| 2008/0089836 A1 | 4/2008 | Hainfeld |
| 2010/0166664 A1 | 7/2010 | Butts et al. |
| 2010/0166665 A1 | 7/2010 | Butts et al. |
| 2010/0297019 A1 | 11/2010 | Lanza et al. |
| 2011/0097277 A1 | 4/2011 | Jiang et al. |
| 2011/0213192 A1 | 9/2011 | Levy et al. |

FOREIGN PATENT DOCUMENTS

WO    WO2007146680 A1    12/2007

OTHER PUBLICATIONS

Starck et al., "Surface Chemistry and Rehology of Polysulfobetaine-Coated Silica", Langmuir, vol. 23, No. 14, pp. 7587-7593, 2007.
Choi et al., "Renal Clearance of Quantum Dots", Nature Biotechnology, Letters, vol. 25, No. 10, Oct. 2007.
Ding et al., "Reversible Assembly and Disassembly of Gold Nanoparticles Directed by a Zwitterionic Polymer", Chem. Eur. J., vol. 13, pp. 4197-4202, 2007.

*Primary Examiner* — Brian-Yong Kwon
*Assistant Examiner* — Kauser M Akhoon
(74) *Attorney, Agent, or Firm* — Andrew J. Caruso

(57) ABSTRACT

The present invention provides a trialkoxysilanes having structure I

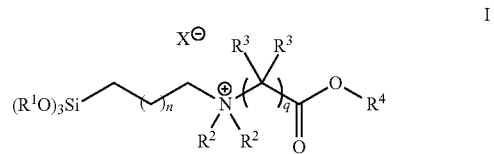

wherein $R^1$ and $R^2$ are independently at each occurrence a $C_1$-$C_3$ alkyl group; $R^3$ is independently at each occurrence a hydrogen or a $C_1$-$C_3$ alkyl group; $R^4$ is a $C_1$-$C_5$ aliphatic radical, a $C_7$-$C_{12}$ aromatic radical, or a $C_5$-$C_{10}$ cycloaliphatic group; n is 0, 1, 2 or 3; q is 1, 2 or 3; and $X^-$ represents a charge balancing counterion. The trialkoxysilanes are useful for the preparation of nanoparticulate diagnostic imaging agent compositions.

6 Claims, No Drawings

NANOPARTICULATE COMPOSITIONS FOR DIAGNOSTIC IMAGING

BACKGROUND

This application relates generally to nanoparticulate compositions useful as diagnostic imaging agents for use in one or more of X-ray/Computed Tomography (CT) and Magnetic Resonance Imaging (MRI). More particularly, the application relates to nanoparticulate compositions useful as contrast agents, and methods for making and using such agents.

Almost all clinically approved diagnostic contrast agents are compositions comprising small molecules. Relatively small, iodinated aromatic compounds have served as the standard contrast agents in X-ray and CT, while Gd-chelates are used for Magnetic Resonance Imaging. Known contrast agents suffer from one or more disadvantages such as overly rapid clearance from the body, overly long retention within the body, toxicity, nonspecificity, instability, and high cost. Such limitations work to reduce the overall effectiveness of a program of therapy relying on diagnostic imaging. Despite considerable progress made in this field to date there remains a need for new classes of contrast agents which overcome one or more of these disadvantages and/or which possess characteristics which enable new modes of diagnostic imaging.

Nanoparticulate compositions show considerable promise in medical applications, both diagnostic and therapeutic. While only a few nanoparticulate composition-containing agents have been clinically approved for magnetic resonance imaging applications and for drug delivery applications, hundreds of such agents are still in development. There is substantial evidence that nanoparticulate compositions have benefits over currently used small molecule agents in terms of efficacy for diagnostics and therapeutics. However, the effect of particle size, structure, and surface properties on the in-vivo bio-distribution and clearance of nanoparticulate composition-based agents is not well understood. Nanoparticles, depending on their size, tend to stay in the body for longer periods compared to small molecules. In the case of contrast agents, it is preferred to have maximum renal clearance of the agents from the body with minimum short term or long term toxicity.

Thus there is a need for new nanoparticulate compositions for use as contrast agents and/or imaging agents with improved properties. In particular, nanoparticulate compositions having improved characteristics related to renal clearance and toxicity would be especially advantageous. In addition, there is a need for novel synthetic intermediates with which to prepare such nanoparticulate compositions.

BRIEF DESCRIPTION

In a first aspect, the present invention provides a trialkoxysilane having structure I

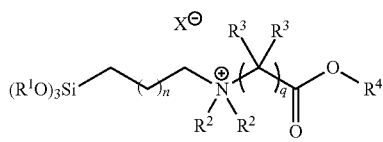

wherein $R^1$ and $R^2$ are independently at each occurrence a $C_1$-$C_3$ alkyl group; $R^3$ is independently at each occurrence a hydrogen or a $C_1$-$C_3$ alkyl group; $R^4$ is a $C_1$-$C_5$ aliphatic radical, a $C_7$-$C_{12}$ aromatic radical, or a $C_5$-$C_{10}$ cycloaliphatic group; n is 0, 1, 2 or 3; q is 1, 2 or 3; and $X^-$ represents a charge balancing counterion.

In a second aspect, the present invention provides a nanoparticle composition comprising nanoparticles having idealized structure II, the nanoparticles comprising a functionalized nanoparticulate metal oxide and a positively charged trioxysilane ligand

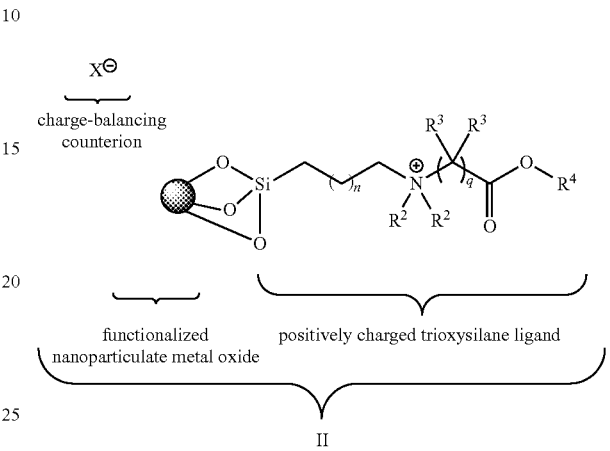

wherein $R^2$ is independently at each occurrence a $C_1$-$C_3$ alkyl group; $R^3$ is independently at each occurrence a hydrogen or a $C_1$-$C_3$ aliphatic group; $R^4$ is a $C_1$-$C_5$ aliphatic radical, a $C_7$-$C_{12}$ aromatic radical, or a $C_5$-$C_{10}$ cycloaliphatic group; n is 0, 1, 2 or 3; q is 1, 2 or 3; $X^-$ represents a charge balancing counterion; and the functionalized nanoparticulate metal oxide comprises nanoparticulate tantalum oxide.

In a third aspect, the present invention provides a nanoparticle composition comprising nanoparticles having idealized structure III, the nanoparticles comprising a functionalized nanoparticulate metal oxide and a trioxysilane betaine ligand

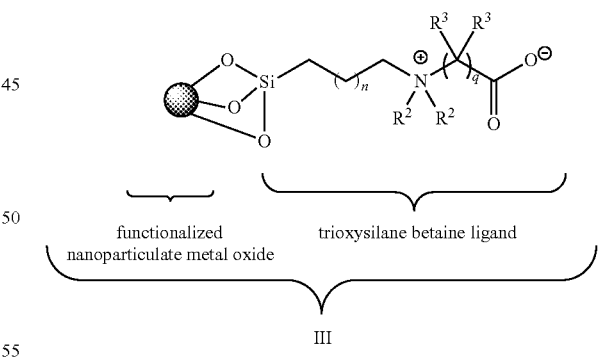

wherein $R^2$ is independently at each occurrence a $C_1$-$C_3$ alkyl group; $R^3$ is independently at each occurrence a hydrogen or a $C_1$-$C_3$ alkyl group; n is 0, 1, 2 or 3; q is 1, 2 or 3; and the functionalized nanoparticulate metal oxide comprises nanoparticulate tantalum oxide In yet a fourth aspect, the present invention provides diagnostic imaging agent composition comprising nanoparticles having idealized structure III, the nanoparticles comprising a functionalized nanoparticulate metal oxide and a trioxysilane betaine ligand

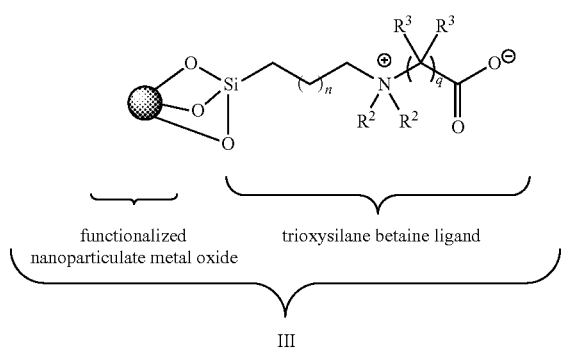

⎧functionalized⎫  ⎧trioxysilane betaine ligand⎫
⎩nanoparticulate metal oxide⎭

III wherein $R^2$ is independently at each occurrence a $C_1$-$C_3$ alkyl group; $R^3$ is independently at each occurrence a hydrogen or a $C_1$-$C_3$ alkyl group; n is 0, 1, 2 or 3; q is 1, 2 or 3; and the functionalized nanoparticulate metal oxide comprises nanoparticulate tantalum oxide.

DETAILED DESCRIPTION

In the following specification and the claims, which follow, reference will be made to a number of terms, which shall be defined to have the following meanings.

The singular forms "a", "an", and "the" include plural referents unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthracenyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3$)$_2$PhO—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e., 4-Br$CH_2CH_2CH_2$Ph-), and the like. Further examples of aromatic radicals include 4-allyloxyphen-1-oxy, 4-aminophen-1-yl (i.e., 4-$H_2$NPh-), 3-aminocarbonylphen-1-yl (i.e., $NH_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPh$CH_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh($CH_2$)$_6$PhO—), 4-hydroxymethylphen-1-yl (i.e., 4-HO$CH_2$Ph-), 4-mercaptomethylphen-1-yl (i.e., 4-HS$CH_2$Ph-), 4-methylthiophen-1-yl (i.e., 4-$CH_3$SPh-), 3-methoxyphen-1-yl, 2-methoxycarbonylphen-1-yloxy (e.g., methyl salicyl), 2-nitromethylphen-1-yl (i.e., 2-$NO_2CH_2$Ph), 3-trimethylsilylphen-1-yl, 4-t-butyldimethylsilylphen-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropy-lidene-2,2-bis(cyclohex-4-yl) (i.e., —$C_6H_{10}C(CF_3)_2$ $C_6H_{10}$—), 2-chloromethylcyclohex-1-yl, 3-difluoromethyl-enecyclohex-1-yl, 4-trichloromethylcyclohex-1-yloxy, 4-bromodichloromethylcyclohex-1-ylthio, 2-bromoethylcy-clopent-1-yl, 2-bromopropylcyclohex-1-yloxy (e.g., $CH_3CHBrCH_2C_6H_{10}O$—), and the like. Further examples of cycloaliphatic radicals include 4-allyloxycyclohex-1-yl, 4-aminocyclohex-1-yl (i.e., $H_2C_6H_{10}$—), 4-aminocarbonyl-cyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopro-pylethenyl, 3-formyl-2-terahydrofuranyl, 2-hexyl-5-tetrahy-drofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycar-bonylcyclohex-1-yloxy (2-$CH_3OCOC_6H_{10}O$—), 4-nitrom-ethylcyclohex-1-yl (i.e., $NO_2CH_2C_6H_{10}$—), 3-trimethylsi-lylcyclohex-1-yl, 2-t-butyldimethylsilylcyclopent-1-yl, 4-trimethoxysilylethylcyclohex-1-yl (e.g., $(CH_3O)_3$ $SiCH_2CH_2C_6H_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Ali-phatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-meth-ylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Ali-phatic radicals comprising one or more halogen atoms include the alkyl halides trifluoromethyl, bromodifluorom-ethyl, chlorodifluoromethyl, hexafluoroisopropylidene, chlo-romethyl, difluorovinylidene, trichloromethyl, bromodichlo-romethyl, bromoethyl, 2-bromotrimethylene (e.g., —$CH_2CHBrCH_2$—), and the like. Further examples of ali-phatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hex-amethylene, hydroxymethyl (i.e., —$CH_2OH$), mercaptom-ethyl (i.e., —$CH_2SH$), methylthio (i.e., —$SCH_3$), methylthi-omethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-tri-methoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

In one embodiment, the present invention provides a tri-alkoxysilane having structure I

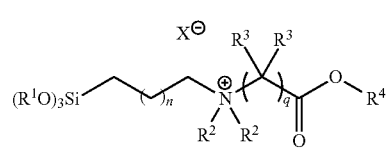

wherein $R^1$ and $R^2$ are independently at each occurrence a $C_1$-$C_3$ alkyl group; $R^3$ is independently at each occurrence a hydrogen or a $C_1$-$C_3$ alkyl group; $R^4$ is a $C_1$-$C_5$ aliphatic radical, a $C_7$-$C_{12}$ aromatic radical, or a $C_5$-$C_{10}$ cycloaliphatic group; n is 0, 1, 2 or 3; q is 1, 2 or 3; and $X^-$ represents a charge balancing counterion. As is demonstrated in this disclosure, trialkoxysilanes falling within the scope of generic structure I are useful in the preparation of nanoparticulate compositions useful as contrast agents in medical imaging.

Trialkoxysilane I may be reacted with nanoparticulate metal oxides through the agency of the trialkoxysilyl group to form coated nanoparticulate metal oxides in which the ligand corresponding to structure I is bound to the nanoparticulate metal oxide through one or more silicon oxygen bonds.

Referring to trialkoxysilane having structure I, $R^1$ and $R^2$ are independently at each occurrence a $C_1$-$C_3$ alkyl group, for example a methyl group, an ethyl group, an isopropyl group, or a propyl group. The nitrogen shown in structure I is bound to four different carbon atoms and represents the positively charged component of a quaternary ammonium salt. The group $R^3$ may be independently at each occurrence hydrogen, or a $C_1$-$C_3$ alkyl group. In one or more embodiments, each $R^3$ is hydrogen. The group $R^4$ is a protecting group which may be removed under mild conditions, for example under mildly acidic conditions, or $R^4$ is a protecting group that may be removed under mild hydrogenolysis conditions. Ester pro-tecting groups which may be removed under mildly acidic conditions include but are not limited to tertiary butyl groups, tetrahydropyranyl groups, methylthiomethylene groups, 1-methyl-1-cyclopentyl groups, and 1-methyl-1-cyclohexyl groups. Ester protecting groups which may be removed under mild hydrogenolysis conditions include but are not limited to benzyl groups, p-methoxybenxyl groups, and p-alkylbenzyl groups.

Trialkoxysilane compounds having structure I are illus-trated by specific examples 1a-1o in Table I below. Those of ordinary skill in the art and having read this disclosure will understand how such compounds may be prepared. For example, a protected ester compound comprising a reactive leaving group may be reacted with a trialkoxysilane compris-ing a tertiary amine group. The tertiary amine group of the trialkoxysilane reacts with the protected ester compound comprising a reactive leaving group thereby transforming the tertiary amine nitrogen into a quaternary nitrogen. Com-pounds 1a-1d, 1i-1k, and 1m-1o illustrate trialkoxysilanes provided by the present invention wherein the group $R^4$ is an acid sensitive protecting group. Compounds 1e-1h, and 1l illustrate trialkoxysilanes provided by the present invention wherein the group $R^4$ is protecting group (benzyl) which may be removed under mild hydrogenolysis conditions, e.g. exposure to hydrogen gas under conditions of ambient pressure and temperature in the presence of palladium on carbon. It should be noted that other protecting groups which may be removed under hydrogenolytic conditions are also suitable, for example, the p-methylbenzyl group, the p-bromobenzyl group, and the p-fluorobenzyl group.

In Table 1, the charge balancing counterion $X^-$ of structure I is illustrated by bromide ($Br^-$), iodide ($I^-$), tosylate ($TsO^-$), mesylate ($MsO^-$), acetate ($AcO^-$), bicarbonate ($HCO_3^-$) and trifluoromethanesulfonate ($Tf^-$), though a host of organic and inorganic anions may be suitable as well.

TABLE I

Examples of Trialkoxysilanes Having Structure I

| Entry | Structure | $R^1$ | $R^2$ | $R^3$ | $R^4$ | X- | n | q |
|---|---|---|---|---|---|---|---|---|
| 1a | (EtO)₃Si-(CH₂)₃-N⁺(CH₃)₂-CH₂-C(=O)-O-t-Bu, Br⁻ | Et | CH₃ | H | t-Bu | Br⁻ | 1 | 1 |
| 1b | (EtO)₃Si-(CH₂)₃-N⁺(CH₃)(Et)-CH₂-C(=O)-O-t-Bu, Br⁻ | Et | CH₃, Et | H | t-Bu | Br⁻ | 1 | 1 |
| 1c | (EtO)₃Si-(CH₂)₃-N⁺(CH₃)(Et)-CH₂-C(=O)-O-t-Bu, TsO⁻ | Et | CH₃, Et | H | t-Bu | TsO⁻ | 1 | 1 |
| 1d | (EtO)₃Si-(CH₂)₃-N⁺(CH₃)₂-CH₂-C(=O)-O-(1-methylcyclopentyl), MsO⁻ | Et | CH₃ | H | 1-methylcyclopentyl | MsO⁻ | 1 | 1 |
| 1e | (EtO)₃Si-(CH₂)₃-N⁺(CH₃)₂-CH₂-C(=O)-O-CH₂-Ph, AcO⁻ | Et | CH₃ | H | CH₂Ph | AcO⁻ | 1 | 1 |
| 1f | (EtO)₃Si-(CH₂)₃-N⁺(CH₃)₂-CH₂-C(=O)-O-CH₂-Ph, CF₃SO₃⁻ | Et | CH₃ | H | CH₂Ph | Tf | 1 | 1 |
| 1g | (EtO)₃Si-(CH₂)₃-N⁺(CH₃)₂-(CH₂)₃-C(=O)-O-CH₂-Ph, CF₃SO₃⁻ | Et | CH₃ | H | CH₂Ph | Br⁻ | 1 | 3 |
| 1h | (EtO)₃Si-CH₂-N⁺(CH₃)₂-(CH₂)₃-C(=O)-O-CH₂-Ph, Br⁻ | Et | CH₃ | H | CH₂Ph | Br⁻ | 0 | 3 |
| 1i | (EtO)₃Si-CH₂-N⁺(CH₃)₂-CH₂-C(=O)-O-(tetrahydropyranyl), I⁻ | Et | CH₃ | H | THP | I⁻ | 0 | 1 |

TABLE I-continued

Examples of Trialkoxysilanes Having Structure I

| Entry | Structure | R¹ | R² | R³ | R⁴ | X⁻ | n | q |
|---|---|---|---|---|---|---|---|---|
| 1j | (MeO)₃Si-CH₂CH₂-N⁺(CH₃)(CH₃)-CH₂-C(O)-O-THP, Br⁻ | CH₃ | CH₃ | H | THP | Br⁻ | 0 | 1 |
| 1k | (MeO)₃Si-CH₂CH₂-N⁺(CH₂CH₃)(CH₃)-CH₂-C(O)-O-CH₂-S-CH₃, Br⁻ | CH₃ | Et | H | MTM | Br⁻ | 0 | 1 |
| 1l | (EtO)₃Si-(CH₂)₃-N⁺(CH₃)(CH₃)-C(CH₃)₂-C(O)-O-CH₂-Ph, Br⁻ | Et | CH₃ | CH₃ | CH₂Ph | Br⁻ | 1 | 1 |
| 1m | (EtO)₃Si-(CH₂)₃-N⁺(CH₃)(CH₃)-C(CH₃)₂-C(O)-O-t-Bu, Br⁻ | Et | CH₃ | CH₃ | t-Bu | Br⁻ | 1 | 1 |
| 1n | (CH₃O)₃Si-(CH₂)₂-N⁺(CH₃)(CH₃)-CH₂-C(O)-O-t-Bu, Br⁻ | CH₃ | CH₃ | H | t-Bu | Br⁻ | 2 | 1 |
| 1o | (CH₃O)₃Si-(CH₂)₂-N⁺(CH₃)(CH₃)-CH₂-C(O)-O-C(CH₃)₂CH₂CH₃, HCO₃⁻ | CH₃ | CH₃ | H | 2-methyl-2-butyl | HCO₃⁻ | 2 | 1 |

In one or more embodiments, the present invention provides a trialkoxysilane falling within the scope of generic structure I wherein each $R^1$ and each $R^2$ are methyl, each $R^3$ is hydrogen, and $R^4$ is tertiary butyl, for example compound 1n of Table I.

In one or more alternate embodiments, the present invention provides a trialkoxysilane falling within the scope of generic structure I wherein each $R^1$ is ethyl and each $R^2$ is methyl, each $R^3$ is methyl, and $R^4$ is tertiary butyl, for example compound 1m of Table I.

In one or more additional embodiments, the present invention provides a trialkoxysilane falling within the scope of generic structure I wherein each $R^1$ and each $R^2$ are methyl, each $R^3$ is hydrogen, and $R^4$ is 2-methyl-2-butyl, for example compound 1o of Table I.

In one embodiment, the present invention provides a trialkoxysilane falling within generic structure I wherein $R^4$ is benzyl, for example compounds 1e-1h, and 1l of Table I. In an alternate embodiment, $R^4$ is p-methoxybenzyl.

As noted, trialkoxysilanes I are useful in the preparation of nanoparticles, which are themselves useful as contrast media in medical diagnostic imaging. The trialkoxysilane moiety $(R^1O)_3Si$ present in trialkoxysilane I can be caused to condense with reactive oxygen-containing groups of a nanoparticulate metal oxide such as nanoparticulate tantalum oxide thereby coating the surface of the nanoparticulate metal oxide to provide a nanoparticulate composition comprising a functionalized nanoparticulate metal oxide and a positively charged trioxysilane ligand. The structures of such functionalized nanoparticulate metal oxides may be complex and contain a plurality of trioxysilane ligands bound to the nanoparticulate metal oxide particles. The term "functionalized" when used in the context of the present invention may be taken to mean "coated" or "partially coated" and wherein at least a portion of the trioxysilane ligands "coating" the nanoparticulate metal oxide are actually chemically bound via one or more oxygen-silicon bonds to the nanoparticulate metal oxide.

Under certain circumstances, nanoparticles provided by the present invention comprising trioxysilane ligands corresponding to trialkoxysilane I, may additionally comprise trioxysilane ligands corresponding to trialkoxysilane Ia

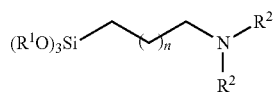

Ia which comprises a tertiary amine moiety and wherein $R^1$ and $R^2$ are independently at each occurrence a $C_1$-$C_3$ alkyl group; and n is 0, 1, 2 or 3.

The presence of such trioxysilane ligands corresponding to tertiary amine 1a in nanoparticles may affect the performance characteristics of such nanoparticles as a diagnostic imaging agents, and may also affect the toxicity characteristics of such nanoparticles. In certain embodiments, nanoparticles provided by the present invention comprise both trioxysilane ligands corresponding to trialkoxysilane I and trioxysilane ligands corresponding to trialkoxysilane Ia. In one embodiment, less than 50 percent of the trioxysilane ligands present in a nanoparticle provided by the present invention correspond to trialkoxysilane Ia. In another embodiment, less than 20 percent of the trioxysilane ligands present in a nanoparticle provided by the present invention correspond to trialkoxysilane Ia. In yet another embodiment, less than 5 percent of the trioxysilane ligands present in a nanoparticle provided by the present invention correspond to trialkoxysilane Ia. In an alternate embodiment, the nanoparticle provided by the present invention is substantially free of trioxysilane ligands corresponding to trialkoxysilane Ia.

For convenience, functionalized nanoparticulate compositions are frequently shown as a spherical body representing the nanoparticulate metal oxide bound to a single trioxysilane ligand of approximately the same size. In reality, the nanoparticulate metal oxide particles are considerably larger than the associated plurality of trioxysilane ligands bound to each nanoparticulate metal oxide particle in the composition. In addition, multiple condensation pathways are possible as the trialkoxysilane I is condensed with reactive oxygen-containing groups of the nanoparticulate metal oxide. Notwithstanding this significant idealization in the chemical representation of the nanoparticulate composition, those of ordinary skill in the art will appreciate the nature and chemical structures of the nanoparticulate compositions provided by the present invention and how these structures differ from known nanoparticulate compositions. When the chemical structure of a nanoparticulate composition has been simplified in one or more respects, it is at times herein referred to as having an idealized structure.

In one embodiment, the present invention provides a nanoparticulate composition comprising nanoparticles having idealized structure II, the nanoparticles comprising a functionalized nanoparticulate metal oxide and a positively charged trioxysilane ligand

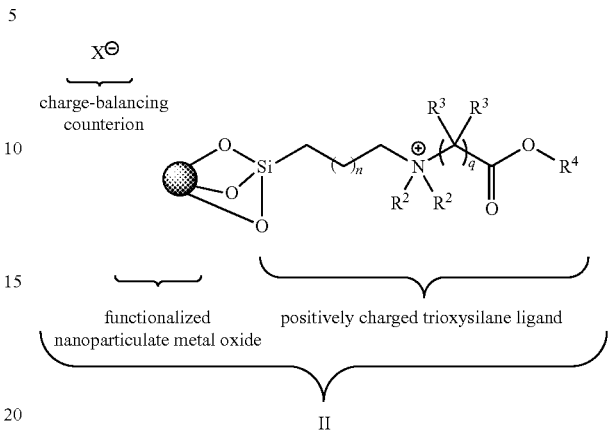

II wherein $R^2$ is independently at each occurrence a $C_1$-$C_3$ alkyl group; $R^3$ is independently at each occurrence a hydrogen or a $C_1$-$C_3$ alkyl group; $R^4$ is a $C_1$-$C_5$ aliphatic radical, a $C_7$-$C_{12}$ aromatic radical, or a $C_5$-$C_{10}$ cycloaliphatic group; n is 0, 1, 2 or 3; q is 1, 2 or 3; $X^-$ represents a charge balancing counterion; and the functionalized nanoparticulate metal oxide comprises nanoparticulate tantalum oxide.

Each of the nanoparticulate compositions provided by the present invention comprises a nanoparticulate metal oxide comprising tantalum oxide ($Ta_2O_5$). In one or more embodiments, the nanoparticulate metal oxide comprising tantalum oxide ($Ta_2O_5$) comprises other metal oxides, for example iron oxide and titanium oxide, in addition to the $Ta_2O_5$. Typically, however, the amount of these additional metal oxides is small relative to the amount of tantalum oxide present in the nanoparticulate metal oxide. In one embodiment, the nanoparticulate metal oxide used according to one or more aspects of the present invention is about 90% by weight tantalum oxide. In another embodiment, the nanoparticulate metal oxide used according to one or more aspects of the present invention is about 95% by weight tantalum oxide. In one embodiment, the nanoparticulate metal oxide is said to consist essentially of tantalum oxide and contains less than 1% by weight of other metal oxide species.

Nanoparticulate compositions comprising nanoparticles having idealized structure II are illustrated in Table II and correspond to the condensation product of a nanoparticulate metal oxide comprising tantalum oxide with a trialkoxysilane compound having structure I. For purposes of illustration, each of the trialkoxysilane compounds listed in Table I is shown as transformed into the corresponding trioxysilane ligand bound to the functionalized nanoparticulate metal oxide in Table II. Thus, structure 1a of Table I corresponds to structure 2a of Table II, structure 1b of Table I corresponds to structure 2b of Table II and so forth. Each of the structures given in Table II has been idealized for convenience. Those of ordinary skill in the art and having read this disclosure will understand that the identity of the charge-balancing counterion in a given composition may depend upon reaction protocols employed in the preparation of the nanoparticulate composition comprising nanoparticles II.

TABLE II
Examples of Nanoparticles Having Idealized Structure II
| Entry | Structure | R² | R³ | R⁴ | X– | n | q |
|---|---|---|---|---|---|---|---|
| 2a | 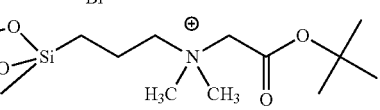 | CH₃ | H | t-Bu | Br⁻ | 1 | 1 |
| 2b | 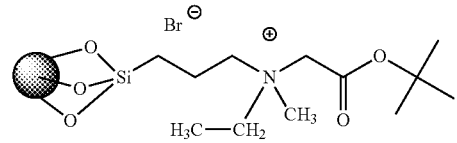 | CH₃, Et | H | t-Bu | Br⁻ | 1 | 1 |
| 2c | 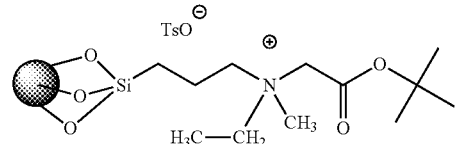 | CH₃, Et | H | t-Bu | TsO⁻ | 1 | 1 |
| 2d | 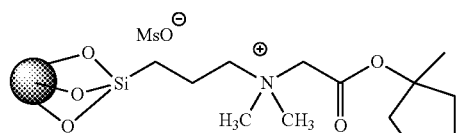 | CH₃ | H |  | MsO⁻ | 1 | 1 |
| 2e | 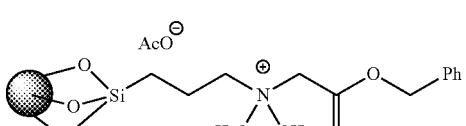 | CH₃ | H |  | AcO⁻ | 1 | 1 |
| 2f | 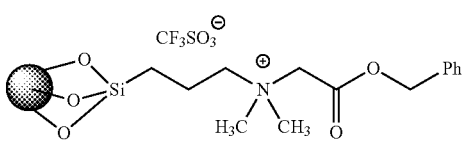 | CH₃ | H |  | Tf | 1 | 1 |
| 2g | 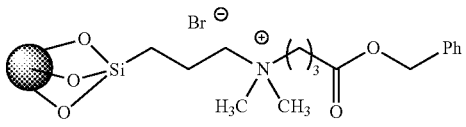 | CH₃ | H |  | Br⁻ | 1 | 3 |
| 2h | 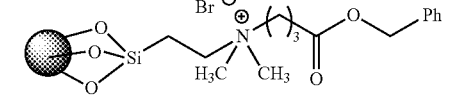 | CH₃ | H |  | Br⁻ | 0 | 3 |
| 2i | 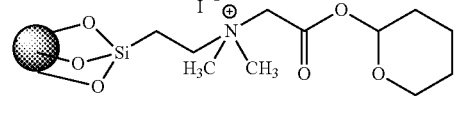 | CH₃ | H | THP | I⁻ | 0 | 1 |
| 2j | 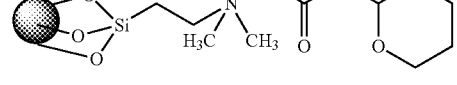 | CH₃ | H | THP | Br⁻ | 0 | 1 |

TABLE II-continued

Examples of Nanoparticles Having Idealized Structure II

| Entry | Structure | $R^2$ | $R^3$ | $R^4$ | X- | n | q |
|---|---|---|---|---|---|---|---|
| 2k | 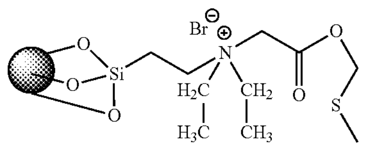 | Et | H | MTM | Br⁻ | 0 | 1 |
| 2l | 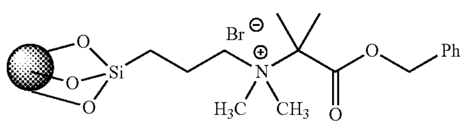 | $CH_3$ | $CH_3$ | benzyl | Br⁻ | 1 | 1 |
| 2m | 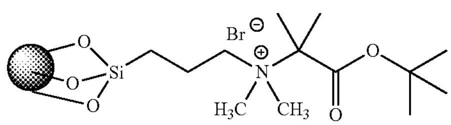 | $CH_3$ | $CH_3$ | t-Bu | Br⁻ | 1 | 1 |
| 2n | 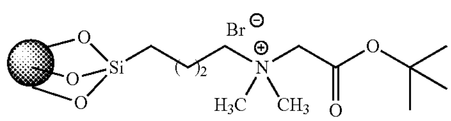 | $CH_3$ | H | t-Bu | Br⁻ | 2 | 1 |
| 2o | 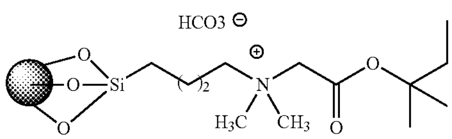 | $CH_3$ | H | | $HCO_3^-$ | 2 | 1 |

In one or more embodiments, the present invention provides a nanoparticulate composition comprising nanoparticles falling within the scope of generic structure II wherein each $R^2$ is methyl, each $R^3$ is hydrogen, and $R^4$ is tertiary butyl, for example compounds 2a and 2n of Table II.

In one or more alternate embodiments, the present invention provides a nanoparticulate composition comprising nanoparticles falling within the scope of generic structure II wherein each $R^2$ is methyl, each $R^3$ is hydrogen, and $R^4$ is 2-methyl-2-butyl, for example nanoparticle 2o of Table II.

In one embodiment, the present invention provides a nanoparticulate composition comprising nanoparticles falling within generic structure II wherein $R^4$ is benzyl, for example compounds 2e-2h, and 2l of Table II. In an alternate embodiment, $R^4$ is p-methoxybenzyl.

In one embodiment, the present invention provides a nanoparticulate composition comprising nanoparticles falling within generic structure II wherein each $R^2$ is methyl, each $R^3$ is hydrogen, $R^4$ is tertiary butyl, n is 1, q is 1; and the nanoparticulate metal oxide consists essentially of nanoparticulate tantalum oxide. See for example the nanoparticle having idealized structure 2a.

In one aspect, nanoparticulate compositions comprising nanoparticles falling within generic structure II are primarily useful as precursors to nanoparticulate compositions comprising trioxysilane betaine ligands such as shown in idealized structure III

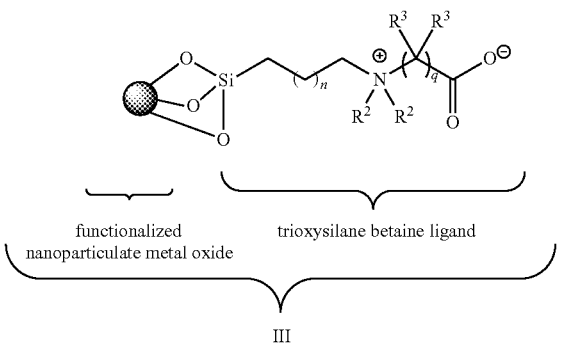

functionalized nanoparticulate metal oxide trioxysilane betaine ligand

III wherein $R^2$ is independently at each occurrence a $C_1$-$C_3$ alkyl group; $R^3$ is independently at each occurrence a hydrogen or a $C_1$-$C_3$ alkyl group; n is 0, 1, 2 or 3; q is 1, 2 or 3; and the functionalized nanoparticulate metal oxide comprises nanoparticulate tantalum oxide. Such nanoparticulate compositions show promise as contrast agents in medical diagnostic imaging.

Those of ordinary skill in the art and having read his disclosure will understand that cleavage of the ester moiety comprising the protecting group $R^4$ provides a carboxylate moiety which can serve as the charge balancing counterion to the positively charged quaternary nitrogen. Such charge separated, but charged balanced species are referred to as betaines in organic chemistry.

Table III provides examples of nanoparticulate compositions comprising nanoparticles falling within generic structure III and which comprise a functionalized nanoparticulate metal oxide and a trioxysilane betaine ligand.

TABLE III

Examples of Nanoparticles Having Idealized Structure III

| Entry | Structure | $R^2$ | $R^3$ | n | q |
|---|---|---|---|---|---|
| 3a | 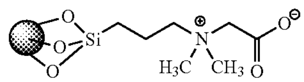 | $CH_3$ | H | 1 | 1 |
| 3b | 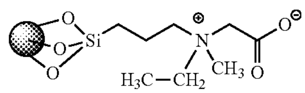 | $CH_3$, Et | H | 1 | 1 |
| 3c | 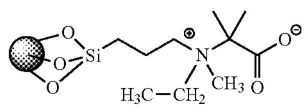 | $CH_3$, Et | $CH_3$ | 1 | 1 |
| 3d | 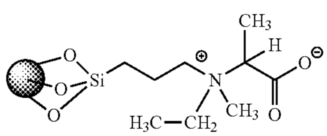 | $CH_3$, Et | $CH_3$ | 1 | 1 |
| 3e | 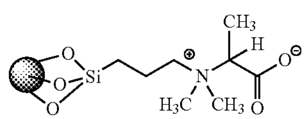 | $CH_3$ | $CH_3$, H | 1 | 1 |
| 3f | 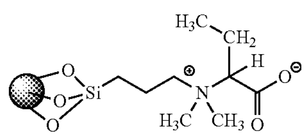 | $CH_3$ | Et, H | 1 | 1 |
| 3g | 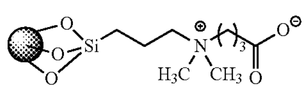 | $CH_3$ | H | 1 | 3 |
| 3h | 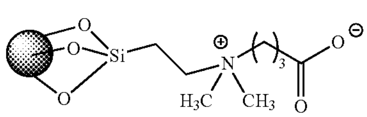 | $CH_3$ | H | 0 | 3 |
| 3i | 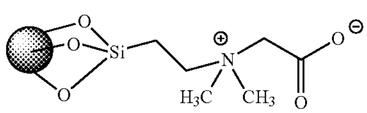 | $CH_3$ | H | 0 | 1 |
| 3j | 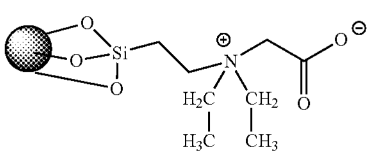 | Et | H | 0 | 1 |
| 3k | 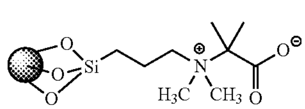 | $CH_3$ | $CH_3$ | 1 | 1 |
| 3l | 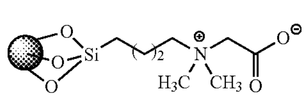 | $CH_3$ | H | 2 | 1 |
| 3m | | $CH_3$ | $CH_3$ | 2 | 1 |

In one or more embodiments, the present invention provides a nanoparticulate composition comprising nanoparticles falling within generic structure III wherein each $R^2$ is methyl and each $R^3$ is hydrogen, for example the nanoparticles represented by structures 3a, 3g, 3h, 3i and 3l in Table III.

In one or more alternate embodiments the present invention provides a nanoparticulate composition comprising nanoparticles falling within generic structure III wherein each $R^2$ is methyl and each $R^3$ is methyl, for example the nanoparticles represented by structures 3k and 3m in Table III.

In one or more alternate embodiments the present invention provides a nanoparticulate composition comprising nanoparticles falling within generic structure III wherein n is 1; q is 1; and the functionalized nanoparticulate metal oxide consists essentially of tantalum oxide, for example the nanoparticles represented by structures 3a-3f and 3k in Table III.

In yet another aspect, the present invention provides a diagnostic imaging agent composition comprising nanoparticles having idealized structure III. In one or more embodiments the diagnostic imaging agent composition may comprise a pharmaceutically acceptable carrier and/or excipient. Suitable pharmaceutically acceptable carriers include but are not limited to water, and aqueous ethanol. Suitable pharmaceutically acceptable excipients include but are not limited to salts, disintegrators, binders, fillers, lubricants, and combinations of two or more of the foregoing.

An important characteristic underlying the utility of the diagnostic imaging agent compositions provided by the present invention results from the nanoparticulate nature of the nanoparticles themselves. In one or more embodiments the nanoparticles constituting the diagnostic imaging agent compositions have a median particle size of up to 10 nm. In another embodiment, the nanoparticles constituting the diagnostic imaging agent compositions have a median particle size of up to 6 nm.

EXPERIMENTAL PART

Example 1

Synthesis of Trialkoxysilane 3

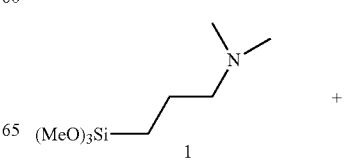

1

19

-continued

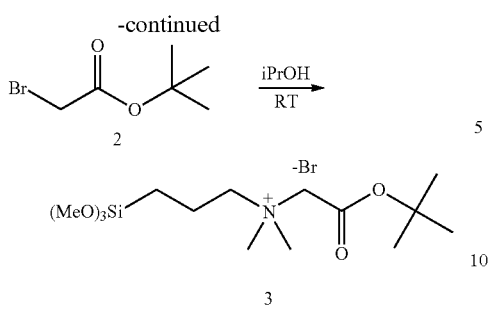

Anhydrous isopropanol (90 mL, Aldrich) and dimethylaminopropyl trimethoxysilane 1 (previously distilled, 26.9 mL, 123.1 mmol, Gelest) were charged to a 250 mL round bottom flask equipped with a stir bar. Bromo-t-butylacetate (Compound 2, 19.1 mL, 129.2 mmol, Aldrich) was added dropwise via syringe. The resultant colorless solution was allowed to stir at room temperature for 22 hours to provide a solution of trialkoxysilane 3 in isopropanol.

Method 1 Preparation of Nanoparticulate Tantalum Oxide ($Ta_2O_5$)

A 2 L, three neck round bottom flask equipped with a stir bar, a nitrogen gas adapter and an addition funnel was flushed with nitrogen gas and charged with anhydrous isopropanol (456 mL), isobutyric acid (7.25 mL, 78.2 mmol, Aldrich) and purified water (6.8 mL, 374.9 mmol). After sparging the solution through a needle for 15 minutes, tantalum ethoxide (25 g, 61.5 mmol) was added dropwise via syringe. The colorless homogeneous solution was allowed to stir at room temperature for 21 hours to provide a solution of nanoparticulate $Ta_2O_5$.

Example 2

Coating Reaction, Synthesis of Nanoparticle 4

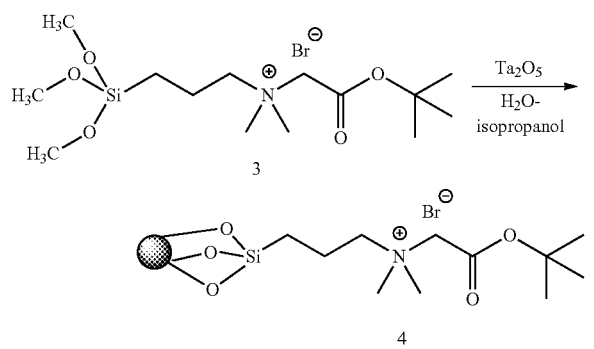

The isopropanol solution containing trialkoxysilane 3 prepared in Example 1 was added dropwise over 40 minutes to the solution of nanoparticulate $Ta_2O_5$ prepared in Method 1. The reaction vessel was fitted with a condenser and heated in an oil bath 75° C. for 2 hours. Purified water (12.4 mL, 1 full equivalent of water for every alkoxy group added to the reaction mixture) was added dropwise via syringe and the mixture was stirred for an additional 3 hours. The temperature was then lowered to 50° C. After 17 hours at 50° C., aqueous $NH_4OH$ (4 molar, 75 mL) solution was added at 50° C. over the course of several minutes. During a time period beginning about 7.5 hours following the addition of the aqueous $NH_4OH$ and ending about 3 hours later, the reaction vessel was swept with nitrogen, and during this time period about 100 mL of isopropanol was entrained from the reaction vessel. Twenty four hours after the addition of $NH_4OH$, the reaction mixture was cooled to room temperature to provide a solution comprising nanoparticles having idealized structure 4.

Example 3

Synthesis of Nanoparticle 5

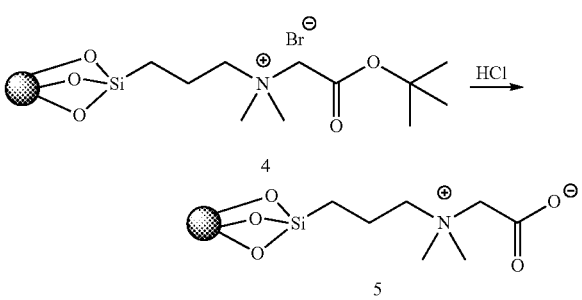

To the solution comprising nanoparticle 4 prepared in Example 2 above was added aqueous HCl (2 molar, 250 mL). The mixture was then heated to 50° C. and stirred for 47 hours over which time period the reaction mixture became heterogeneous. Purified water (100 mL) was then added and the reaction mixture immediately became homogeneous. The temperature was then heated at 75° C. for 48 hours. An aliquot was removed and $^1$H-NMR spectroscopic analysis indicated that the t-butyl ester hydrolysis was complete. The product solution comprising nanoparticles having idealized structure 5 was cooled to room temperature and neutralized with aqueous $NH_4OH$ (120 mL, 4.93M). The nanoparticle having idealized structure 5 is at times herein referred to simply as "CZ2".

Example 4

Purification of Nanoparticle 5

The solution comprising nanoparticle 5 prepared in Example 3 was concentrated on a rotary evaporator to 300 mL and filtered through, in sequence, 450 nm, 100 nm and 20 nm membranes. The filtered solution was further concentrated to 129 g and dialyzed against 2 L of purified water for a total of six cycles using 3.5 kDa MWCO snake skin regenerated cellulose dialysis tubing to afford a solution of the purified product nanoparticle composition comprising nanoparticle 5. An aliquot was freed dried and analyzed spectroscopically. The product yield was 58.3% and was based on the amount of tantalum present in the purified product solution. The Si:Ta mole ratio was found to be 1.49 and the % Ta in the product was 33.5% by weight as determined by elemental analysis. The average particle size ($Z_{effective}$) was found to be 3.1 nm. The particle coating structure assignment was consistent with spectroscopic data.

Method 2 Alternate Preparation of Nanoparticulate Tantalum Oxide ($Ta_2O_5$)

To 364 mL of anhydrous methanol was added 5.36 mL isobutyric acid and 1.495 mL of deuterium oxide at room temperature with stirring in a nitrogen-filled glovebox. This mixture was stirred for 30 min after which tantalum ethoxide (20 g) was added in a drop-wise manner over a period of about 8 min. The reaction mixture was allowed to stir for 5 hours after which time the flask containing the product nanoparticulate $Ta_2O_5$ was removed from the glove box and placed under an inert atmosphere using a Schlenck-/vacuum-line manifold.

Example 5

Synthesis of Nanoparticle 7

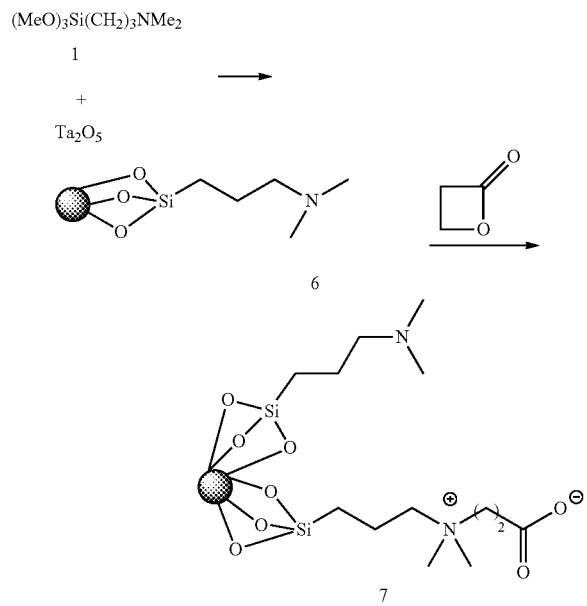

Dimethylaminopropyl trimethoxysilane 1 (11.23 g) was added as a bolus to the nanoparticulate $Ta_2O_5$ prepared in Method 2 above and resultant mixture was refluxed overnight under nitrogen. The reaction mixture was cooled to room temperature to provide a solution comprising nanoparticles 6. Beta-propiolactone (7.95 g) was then added and reaction mixture was stirred overnight at room temperature. Purified water was then added slowly (5.35 mL), and the reaction was stirred overnight at room temperature. The reaction mixture was then brought to pH 10 using 1.73M aqueous sodium hydroxide (about 20-50 mL) and heated to 50° C. for 8 hours. At this point the reaction mixture was allowed to cool to room temperature and stirred overnight. The reaction mixture was neutralized using 1.2M aqueous HCl until a pH of 3 was achieved after which point the reaction mixture stirred for an additional 7 hours at room temperature. The pH was then elevated to 8 using 4M aqueous sodium hydroxide to provide a product solution comprising nanoparticles having idealized structure 7 at times referred to as "CZ1".

Example 5

Purification of Nanoparticle 7 (CZ1)

Exhaustive dialysis using 3.5 kDa MWCO tubing removed small molecular weight impurities. A dialysis bath had a volume of about 3 L and contained four to five tubes each holding 50 mL volume of the product solution. After a total of 21 bath exchanges, the purified product solution was removed from the tubing and further purified by centrifugal filtration through a 30 kDa regenerated cellulose membrane (4 K rpm for 15 min). The reaction yield following purification was 58.3% based on moles of tantalum. The Si:Ta mole ratio was 1.05 as determined by elemental analysis. The average particle size (Zeffective) was found to be 4.8 nm The particle coating structure assignment is consistent with spectroscopic data.

In Vivo Studies

Tantalum oxide nanoparticulate compositions were formulated for injection and tested for endotoxin contamination using commercial kits (Endosafe, Charles River Labs). All agents used for in vivo testing contained no measurable amounts of endotoxin. Each of the nanoparticulate compositions tested had essentially the same nanoparticle size distribution.

Animal studies were performed according to protocols approved by the Institutional Animal Care and Use Committee of GE Global Research. Rats (n=4 per agent and per dose) were injected via tail vein while awake at doses of 400 and 1500 milligrams of Ta per kilogram of body weight. Injected rats were returned to cages and blood samples were taken at multiple timepoints after injection for hematology analysis (complete blood count and clinical chemistry). At seven days post-injection, rats were euthanized using $CO_2$ and organs were harvested for elemental analysis. The quantity of retained Ta was determined per organ and in the total carcass of injected rats by ICP AES.

Representative sections of tissue weighing approximately 500 mg were collected for microwave digestion and subsequent ICP-OES analysis. Samples were transferred quantitatively from VWR® metal-free, sterile, polypropylene 50 mL centrifuge tubes into pre-cleaned 100 mL CEM Corp XP-1500 Plus™ TFM™ Fluoropolymer microwave vessel liners. Tubes were effectively rinsed of residual sample by sequentially adding solvent, vortex agitation and transfer of 2 mL 18 MΩ deionized water (DIW; Millipore, Bedford, Mass., USA), 500 μL HF (46.0-51.0%)+1 mL $HNO_3$ (70%) Ultrex® II ultrapure reagent grade and 2 mL $H_2O_2$ (30-32%) 'Baker Analyzed' ® A.C.S. reagent grade (J.T. Baker, Phillipsburg, N.J., USA). Samples were allowed to pre-digest for 30 minutes at ambient temperature prior to sealing microwave vessel assembly and processing in MARSXpress (CEM Corp, Matthews, N.C., USA) unit ramped to 180° C. in 15 minutes and held for 30 minutes. Vessels were allowed to cool to room temperature prior to depressurization and transfer to pre-weighed 50 mL centrifuge tubes containing 2 mL of 100 ppm Nb in 1% HF as internal standard. Samples were brought to 20 mL total volume using 18 MΩ DIW, rinsing microwave vessel a minimum of 3 times and weighed.

Analyses were carried out under instrumental conditions outlined in Table 1, collected as 3 replicates with spectral conditions of 3 points per peak using 2 point background correction and source equilibration delay of 30 seconds. Matrix-matched standards in 5% $HNO_3$+0.5% HF of 0.2 to 100 ppm from Specpure® 10,000 μg/mL $TaCl_5$ in 2% HF (Alfa Aesar, Ward Hill, Mass., USA) stock were used for calibration and 1 ppm SPEX CertiPrep® Multi-element Solution 4 from stock 10 mg/L (Metuchen, N.J., USA) for quality control. ICP-OES rinse solution of 5% $HNO_3$+0.5% HF was pumped at flow rate 2.0 mL $min^{-1}$ for 45 seconds between each analysis.

TABLE 1

Operational parameters used in the
PerkinElmer Inc. Optima 5300 ™ DV
ICP-OES with radially viewed configuration*

| Parameter | Setting |
|---|---|
| RF generator power (W) | 1450 |
| Plasma gas flow rate (Lmin$^{-1}$) | 15.0 |
| Auxiliary gas flow rate (Lmin$^{-1}$) | 0.20 |
| Nebulizer gas flow rate (Lmin$^{-1}$) | 0.85 |
| Sample flow rate (mLmin$^{-1}$) | 1.50 |
| Wavelengths (nm) | Ta 240.063 |
| | Nb 269.706 |

*Instrument was fitted with a PerkinElmer AS 93 autosampler, 2.0 mm i.d. alumina injector, Ryton Scott Spray Chamber and Gem Tip cross-flow nebulizer sample introduction system.

*Instrument was fitted with a PerkinElmer AS 93 autosampler, 2.0 mm i.d. alumina injector, Ryton Scott Spray Chamber and Gem Tip cross-flow nebulizer sample introduction system.

Organ retention data for four different tantalum nanoparticulate compositions are gathered in Tables 2-4 below. The nanoparticulate compositions referenced in Table 2 (PHS-Ta$_2$O$_5$, structure 8) and Table 3 (ZMS-Ta$_2$O$_5$, structure 9) are provided for purposes of comparison and illustrate the improved performance of contrast agents provided by the present invention illustrative data for which are provided in Table 4.

PHS-Ta$_2$O$_5$, also known as 2-diethylphosphatoethylsilane-TaO, is a nanoparticulate composition comprising nanoparticles having idealized structure 8, and was prepared as described in Investigative Radiology Vol. 47, No. 10, pp 1-10, 2012, a scholarly article which is incorporated by reference herein in its entirety.

8

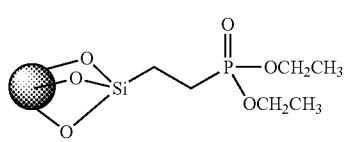

ZMS-Ta$_2$O$_5$, also described as zwitterionic methoxy silane TaO is a nanoparticulate composition comprising nanoparticles having idealized structure 9, was prepared as described in a scholarly article entitled Preclinical Assessment of a Zwitterionic Tantalum Oxide Nanoparticle X-ray Contrast Agent (ACS Nano published online Jul. 25, 2012 (http://www.ncbi.nlm.nih.gov/pubmed/22768795) which article is incorporated by reference herein in its entirety.

9

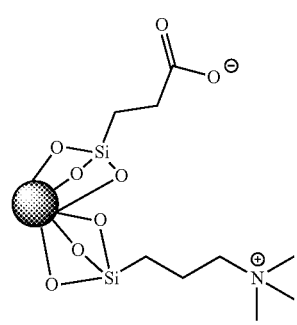

TABLE 2

Retained Ta in organs.
PHS-Ta$_2$O$_5$ seven days following injection

| Tissue | % Injected dose (400 mg Ta/kg dose) +/− SD | % Injected dose (1500 mg Ta/kg dose) +/− SD |
|---|---|---|
| Liver | 2.49 (+/−0.200) | 1.29 (+/−0.090) |
| Kidneys | 2.91 (+/−0.39) | 1.06 (+/−0.10) |
| Spleen | 0.23 (+/−0.020) | 0.14 (+/−0.040) |

TABLE 3

Retained Ta in organs.
ZMS-Ta$_2$O$_5$ seven days following injection

| Tissue | % Injected dose (400 mg Ta/kg dose) +/− SD | % Injected dose (1500 mg Ta/kg dose) +/− SD |
|---|---|---|
| Liver | 0.640 (+/−0.001) | 0.30 (+/−0.010) |
| Kidneys | 0.300 (+/−0.009) | 0.216 (+/−0.009) |
| Spleen | 0.070 (+/−0.0001) | 0.04/−0.0001) |

TABLE 4

Retained Ta in organs.
CZ2 seven days following injection

| Tissue | % Injected dose (400 mg Ta/kg dose) +/− SD | % Injected dose (1500 mg Ta/kg dose) +/− SD |
|---|---|---|
| Liver | 0.081 (+/−0.008) | 0.364 (+/−0.219) |
| Kidneys | 0.225 (+/−0.016) | 0.247 (+/−0.046) |
| Spleen | 0.005 (+/−0.0001) | 0.05/−0.001) |

TABLE 5

Retained Ta in organs.
CZ1 seven days following injection

| Tissue | % Injected dose (400 mg Ta/kg dose) +/− SD | % Injected dose (1500 mg Ta/kg dose) +/− SD |
|---|---|---|
| Liver | 2.53 (+/−0.34) | not determined |
| Kidneys | 0.43 (+/−0.021) | not determined |
| Spleen | 0.26 (+/−0.066) | not determined |

The data presented in Tables 2-5 demonstrate the improved performance of the CZ2 nanoparticulate composition (Table 4, idealized structure 5). Despite being the same size, the different nanoparticulate compositions exhibit very different organ retention profiles. The CZ2 nanoparticulate composition exhibits a much higher rate of organ clearance relative to the control nanoparticulate compositions PHS-Ta$_2$O$_5$ and ZMS-Ta$_2$O$_5$, as well as superior performance relative to the nanoparticulate composition CZ1, a promising sign of potentially enhanced clinical safety and utility for embodiments of the present invention which are substantially free of or contain relatively low levels of tertiary amine-containing trioxysilane ligands corresponding to trialkoxysilane Ia. The nanoparticulate composition CZ1 (idealized structure 7)

comprising a significant percentage (i.e. 50%) of trioxysilane ligands corresponding to trialkoxysilane 1 was sufficiently toxic that organ retention studies could not be successfully carried out at the 1500 mg/kg level.

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of:" Where necessary, ranges have been supplied, those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

What is claimed is:

1. A nanoparticle composition comprising nanoparticles having idealized structure II, the nanoparticles comprising a functionalized nanoparticulate metal oxide and a positively charged trioxysilane ligand

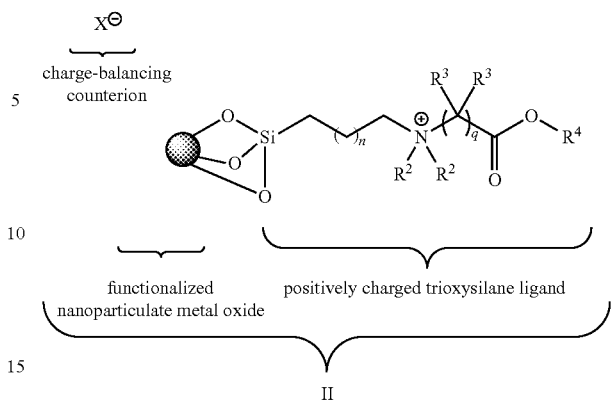

II wherein $R^2$ is independently at each occurrence a $C_1$-$C_3$ alkyl group; $R^3$ is independently at each occurrence a hydrogen or a $C_1$-$C_3$ aliphatic group; $R^4$ is a $C_1$-$C_5$ aliphatic radical, a $C_7$-$C_{12}$ aromatic radical, or a $C_5$-$C_{10}$ cycloaliphatic group; n is 0, 1, 2 or 3; q is 1, 2 or 3; $X^-$ represents a charge balancing counterion; and the functionalized nanoparticulate metal oxide comprises nanoparticulate tantalum oxide.

2. The nanoparticulate composition according to claim 1, wherein each $R^2$ is methyl, each $R^3$ is hydrogen, and $R^4$ is tertiary butyl.

3. The nanoparticulate composition according to claim 1, wherein each $R^2$ is methyl, each $R^3$ is hydrogen, and $R^4$ is 2-methyl-2-butyl.

4. The nanoparticulate composition according to claim 1, wherein $X^-$ represents bromide ion.

5. The nanoparticulate composition according to claim 1, wherein the functionalized nanoparticulate metal oxide consists essentially of tantalum oxide.

6. The nanoparticulate composition according to claim 1, wherein each $R^2$ is methyl, each $R^3$ is hydrogen, $R^4$ is tertiary butyl, n is 1, q is 1; and the nanoparticulate metal oxide consists essentially of nanoparticulate tantalum oxide.

* * * * *